United States Patent
Yamaguchi et al.

(10) Patent No.: US 11,268,962 B2
(45) Date of Patent: Mar. 8, 2022

(54) DEVICE FOR PRETREATMENT OF SAMPLE AND ANALYZER EQUIPPED THEREWITH, AND METHOD FOR PRETREATMENT OF SAMPLE

(71) Applicant: SHIMADZU CORPORATION, Kyoto (JP)

(72) Inventors: Tomoko Yamaguchi, Kyoto (JP); Natsuki Iwata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/551,064

(22) PCT Filed: Feb. 20, 2015

(86) PCT No.: PCT/JP2015/054748
§ 371 (c)(1),
(2) Date: Aug. 15, 2017

(87) PCT Pub. No.: WO2016/132526
PCT Pub. Date: Aug. 25, 2016

(65) Prior Publication Data
US 2018/0031568 A1    Feb. 1, 2018

(51) Int. Cl.
*G01N 33/68* (2006.01)
*G01N 30/04* (2006.01)
(Continued)

(52) U.S. Cl.
CPC .......... *G01N 33/6824* (2013.01); *G01N 1/28* (2013.01); *G01N 1/34* (2013.01); *G01N 1/38* (2013.01); *G01N 30/04* (2013.01); *G01N 33/68* (2013.01); *G01N 35/1009* (2013.01); *G01N 35/1095* (2013.01); *C07K 1/128* (2013.01); *G01N 30/06* (2013.01); *G01N 2001/387* (2013.01); *G01N 2030/067* (2013.01)

(58) Field of Classification Search
CPC ............... G01N 33/68; G01N 33/6824; G01N 35/1009; G01N 35/1095
See application file for complete search history.

(56) References Cited

U.S. PATENT DOCUMENTS

| | | | | |
|---|---|---|---|---|
| 4,155,714 A | * | 5/1979 | Bonner | G01N 33/6824 530/333 |
| 2002/0086442 A1 | * | 7/2002 | Fujiwake | G01N 33/6806 436/518 |
| 2005/0034563 A1 | * | 2/2005 | Richardson | C02F 1/505 75/743 |

FOREIGN PATENT DOCUMENTS

JP    09-068534 A    3/1997

OTHER PUBLICATIONS

Communication dated Oct. 16, 2018, from the European Patent Office in counterpart European Application No. 15882628.9.
(Continued)

*Primary Examiner* — Lyle Alexander
*Assistant Examiner* — Bryan Kilpatrick
(74) *Attorney, Agent, or Firm* — Sughrue Mion, PLLC

(57) ABSTRACT

A sample is dissolved in a reagent 4 containing an organic solvent in a conversion vessel 11. A gas is supplied from a first gas supply part into the conversion vessel 11 via a reagent introduction tube 17, and thus the interior of the conversion vessel 11 is pressurized. A gas is supplied from a second gas supply part into the reagent 4 in the conversion vessel 11 via a reagent discharge tube 18, and thus gas bubbles 41 are formed in the reagent 4.

5 Claims, 5 Drawing Sheets

(51) Int. Cl.
*G01N 1/34* (2006.01)
*G01N 35/10* (2006.01)
*G01N 1/38* (2006.01)
*G01N 1/28* (2006.01)
*C07K 1/12* (2006.01)
*G01N 30/06* (2006.01)

(56) References Cited

OTHER PUBLICATIONS

Communication dated Dec. 16, 2021 from the European Patent Office in Application No. 15882628.9.

* cited by examiner

DEVICE FOR PRETREATMENT OF SAMPLE AND ANALYZER EQUIPPED THEREWITH, AND METHOD FOR PRETREATMENT OF SAMPLE

CROSS REFERENCE TO RELATED APPLICATIONS

This application is a National Stage of International Application No. PCT/JP2015/054748 filed Feb. 20, 2015, the contents of which are incorporated herein by reference in its entirety.

TECHNICAL FIELD

The present invention relates to a device for pretreatment of a sample which dissolves a sample in a reagent containing an organic solvent and introduced into a vessel, an analyzer equipped therewith, and a method for pretreatment of a sample.

BACKGROUND ART

An amino acid sequence analyzer (protein sequencer) utilizing Edman degradation includes an Edman degradation part which configures a device for pretreatment of a sample. In the protein sequencer, Edman degradation in the Edman degradation part causes amino acids to be cleavaged from protein (including peptide) which is a target sample for an amino acid sequence analysis such that amino acid residues are cleavaged one by one as derivatives of amino acids. Each amino acid cleavaged from the protein sample due to Edman degradation is dissolved in a reagent within a vessel called a conversion flask, and then is introduced in a high-performance liquid chromatograph. In the high-performance liquid chromatograph, each amino acid in the reagent is separated while passing through a column and is sequentially detected by a detector, and thus, the amino-acid sequence is analyzed (for example, see Patent Document 1 listed below).

Examples of a reagent used for dissolving a derivatized amino acid (amino acid sample) include an organic solvent such as acetonitrile, and a mixed solution of the organic solvent and water. In the above device for pretreatment of a sample, usually, concentration of the organic solvent is set to a predetermined value. Therefore, depending of the type of the column used in the high-performance liquid chromatograph connected to the device for pretreatment of a sample, concentration of the organic solvent may not be suitable for separation of an amino acid sample. For example, in a case where concentration of the organic solvent is high, an amino acid sample cannot be favorably separated, which may have an adverse effect on the analysis result.

PRIOR ART DOCUMENTS

Patent Documents

Patent Document 1: JP 9-68534 A

SUMMARY OF THE INVENTION

Problems to be Solved by the Invention

In a case where concentration of an organic solvent in a reagent for dissolving an amino acid sample cleavaged by Edman degradation is high as described above, the amino acid sample may be dried by using a centrifugal concentrator, the dried amino acid sample may be dissolved again into another solvent suitable for separation, and measurement may be performed again. However, when the amino acid sample is completely dried in a vessel, the amino acid is precipitated and is likely to adhere to an inner surface of the vessel. Therefore, there is a problem that when the dried amino acid sample is to be dissolved again in the solvent, some acids are not dissolved enough and sample loss occurs.

In addition, work of drying an amino acid sample and dissolving the sample again is usually manually performed by an operator. Therefore, the work takes time and labor, and the work of drying and dissolving again takes time. As a result, there is a problem that an analysis takes a long time.

The present invention is made in view of the above circumstances, and an object of the present invention is to provide a device for pretreatment of a sample which can prevent occurrence of sample loss and can easily and efficiently lower concentration of an organic solvent in a reagent, an analyzer equipped therewith, and a method for pretreatment of a sample.

Means for Solving the Problems

A device for pretreatment of a sample according to the present invention includes a vessel, a reagent introduction part, a reagent discharge part, a first gas supply part, and a second gas supply part. In the vessel, a reagent containing an organic solvent is introduced and a sample is dissolved in the reagent. The reagent introduction part introduces the reagent into the vessel. The reagent discharge part discharges the reagent in which the sample is dissolved in the vessel to an outside of the vessel. The first gas supply part supplies a gas into the vessel and thus pressurizes the interior of the vessel. The second gas supply part supplies a gas into the reagent in the vessel and thus forms gas bubbles in the reagent.

According to such a configuration, a gas is supplied from the second gas supply part to the reagent in the vessel, and thus gas bubbles are formed in the reagent and volatilization of the organic solvent in the reagent is promoted by the gas bubbles. Therefore, concentration of the organic solvent in the reagent can be easily and efficiently lowered. In addition, differing from the configuration of completely drying a sample, since a sample does not adhere to an inner surface of the vessel, occurrence of sample loss can be prevented.

In a case of forming gas bubbles in the reagent as described above, the area of the gas-liquid interface in the reagent increases. Therefore, it is considered that volatilization of the organic solvent is promoted via the interface.

The second gas supply part may supply a gas into the reagent in the vessel via the reagent discharge part.

According to such a configuration, by supplying a gas into the reagent in the vessel via the reagent discharge part for discharging the reagent in which the sample is dissolved to the outside of the vessel, gas bubbles can be formed in the reagent. Since the reagent discharge part is usually configured to discharge a reagent from a bottom portion inside the vessel, gas bubbles can be formed from lower part of the reagent if a gas is supplied into the vessel via the reagent discharge part.

Since gas bubbles can be favorably formed in the reagent in this manner, concentration of the organic solvent in the reagent can be efficiently lowered. In addition, since gas bubbles can be formed in the reagent without adding a new configuration, concentration of the organic solvent in the reagent can be easily lowered without incurring a cost increase.

The first gas supply part may supply a gas into the vessel via the reagent introduction part.

According to such a configuration, by supplying a gas into the vessel via the reagent introduction part for introducing a reagent into the vessel, the interior of the vessel can be pressurized. Since the reagent introduction part is usually configured to introduce a reagent into the vessel by pressure of a gas, the interior of the vessel can be pressurized without newly adding a configuration if a gas is supplied into the vessel via the reagent introduction part. The first gas supply part may supply a gas from a supply source (for example, a gas cylinder) shared by the second gas supply part, or may supply a gas from a supply source different from the supply source of the second gas supply part. In a case where the gas supplied from the first gas supply part is of the same kind as the gas supplied from the second gas supply part, a common supply source may be used. In a case where the gases are of different kinds, different supply sources may be used.

The device for pretreatment of a sample may further include a setting reception processing unit, and a gas supply control unit. The setting reception processing unit receives setting of a time period for supplying a gas from the second gas supply part. The gas supply control unit controls gas supply from the second gas supply part according to the set time period received by the setting reception processing unit.

According to such a configuration, since the time period for supplying a gas from the second gas supply part can be arbitrarily set, the time period for forming gas bubbles in the reagent can be adjusted by adjusting the set time period, and thus concentration of the organic solvent in the reagent can be arbitrarily adjusted. The gas supply control unit may be configured to control gas supply from the first gas supply part in addition to gas supply from the second gas supply part. In this case, the gas supply control unit may control gas supply from the first gas supply part according to the set time received by the setting reception processing unit.

The device for pretreatment of a sample may further include a sample supply part where a protein sample is subjected to Edman degradation. In this case, an amino acid obtained by Edman degradation in the sample supply part may be introduced as a sample into the vessel.

According to such a configuration, in the device for pretreatment of a sample applied to a protein sequencer, occurrence of sample loss can be prevented, and concentration of the organic solvent in the reagent can be easily and efficiently lowered.

An analyzer according to the present invention includes the device for pretreatment of a sample, and a detector which detects a sample in a reagent discharged via the reagent discharge part.

A method for pretreatment of a sample according to the present invention includes a dissolution step, a first gas supply step, and a second gas supply step. In the dissolution step, a reagent containing an organic solvent is introduced into a vessel, and a sample is dissolved in the reagent. In the first gas supply step, a gas is supplied into the vessel, and thus the interior of the vessel is pressurized. In the second gas supply step, a gas is supplied into the reagent in the vessel, and thus gas bubbles are formed in the reagent.

Effects of the Invention

According to the present invention, volatilization of the organic solvent in the reagent is promoted by gas bubbles formed in the reagent. Therefore, concentration of the organic solvent in the reagent can be easily and efficiently lowered. In addition, since the sample does not adhere to the inner surface of the vessel, occurrence of sample loss can be prevented.

MODE FOR CARRYING OUT THE INVENTION

Figure 1:
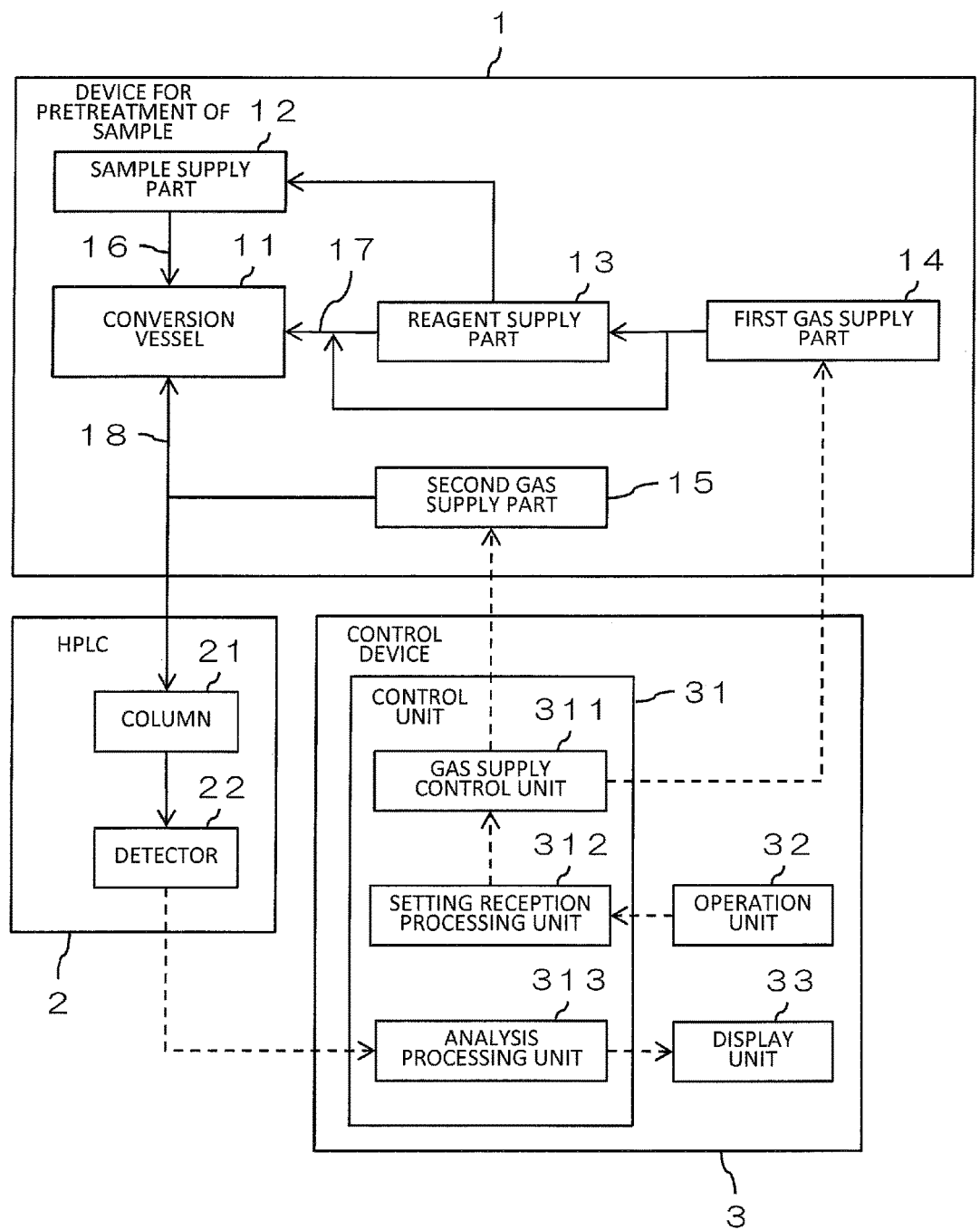
FIG. 1 is a block diagram schematically illustrating a configuration example of an analyzer according to an embodiment of the present invention.

FIG. 1 is a block diagram schematically illustrating a configuration example of an analyzer according to an embodiment of the present invention. In FIG. 1, the flow of a liquid and a gas is indicated by solid arrows, and the flow of electric signals is indicated by broken line arrows.

As an analyzer in which an embodiment of a device for pretreatment of a sample according to the present invention is adopted, the analyzer according to the present embodiment is an amino acid sequence analyzer (protein sequencer) which can utilize Edman degradation to cleavage amino acids from protein (including peptide) that is a target sample for a sequence analysis, and can analyze the amino acid sequence of the target protein (including peptide, the same applies hereinafter). A description will be given below based on a protein sequencer. The protein sequencer includes a device 1 for pretreatment of a sample, a high-performance liquid chromatograph (HPLC) 2, and a control device 3.

The device 1 for pretreatment of a sample includes a conversion vessel 11, a sample supply part 12, a reagent supply part 13, a first gas supply part 14, a second gas supply part 15, and the like. In the device 1 for pretreatment of a sample, the following process is performed. An amino acid is cleavaged from a protein sample by Edman degradation in the sample supply part 12 and the cleavaged amino acid sample is dissolved in a reagent in the conversion vessel 11.

The conversion vessel 11 is a vessel made of, for example, glass. A sample (amino acid sample) is supplied to the conversion vessel 11 from the sample supply part 12, and a reagent is supplied to the conversion vessel 11 from the reagent supply part 13. The first gas supply part 14 supplies an inert gas such as nitrogen gas into the reagent supply part 13, and the pressure of the inert gas causes the reagent to be supplied from the reagent supply part 13. Note that the gas supplied from the first gas supply part 14 is not limited to nitrogen gas as long as the gas is an inert gas, and may be another gas such as helium gas or argon gas.

In the sample supply part 12, a protein sample held by a sample holder (not illustrated) such as a glass fiber filter or a PVDF (polyvinylidene fluoride) membrane is set, and a reagent is supplied from the reagent supply part 13 to the protein sample. The reagent supplied from the reagent supply part 13 to the sample supply part 12 is a reagent necessary for Edman degradation. Examples of the reagent include ethyl acetate, n-butyl chloride, trimethylamine, a PITC n-heptane solution, and trifluoroacetic acid; however, the reagent is not limited to the above.

In the sample supply part 12, the reagent supplied from the reagent supply part 13 is used to cleavage an amino acid from the protein sample by Edman degradation. Specifically, PTC-protein is generated by a coupling reaction and then the N-terminal amino acid of the PTC-protein is cleaved. Thus, the N-terminal amino acid of the protein sample is cleavaged as an ATZ-amino acid. The cleavaged ATZ-amino acid is supplied to the conversion vessel 11 via a sample introduction tube 16. The sample introduction tube 16 configures a sample introduction part fir introducing the amino acid sample (ATZ-amino acid) into the conversion vessel 11.

A reagent is introduced from the reagent supply part 13 via a reagent introduction tube 17 in the conversion vessel 11 into which the amino acid sample (ATZ-amino acid) is supplied. The reagent directly introduced into the conversion vessel 11 from the reagent supply part 13 is of a kind different from the reagent introduced to the sample supply part 12. Examples of the reagent necessary for a conversion reaction from an ATZ-amino acid to a PTH-amino acid include an organic solvent such as acetonitrile, and a mixed solution of the organic solvent and water. The reagent introduction tube 17 configures a reagent introduction part for introducing the reagent containing the organic solvent into the conversion vessel 11.

In the conversion vessel 11, the amino acid sample (ATZ-amino acid) introduced from the sample introduction tube 16 is stabilized, and then is dissolved in the reagent introduced from the reagent introduction tube 17, and is discharged to the HPLC 2 together with the reagent via a reagent discharge tube 18. Specifically, the ATZ-amino acid is converted into a stable PTH-amino acid, and the PTH-amino acid is dissolved in the organic solvent or the mixed solution of the organic solvent and water. The reagent discharge tube 18 configures a reagent discharge part which discharges the reagent in which the amino acid sample (PTH-amino acid) is dissolved to the outside the conversion vessel 11.

The HPLC 2 includes a column 21 and a detector 22. The reagent in which the amino acid sample (PTH-amino acid) is dissolved in the conversion vessel 11 is supplied from the device 1 for pretreatment of a sample to the column 21 via the reagent discharge tube 18, and a sample component is separated while the reagent passes through the column 21. Each sample component separated in the column 21 is detected by the detector 22. Examples of the detector 22 include an ultraviolet-visible detector (UV/VIS detector); however, the detector 22 is not limited to this, and may be another detector such as a photodiode array detector.

In the present embodiment, a gas can be supplied from the first gas supply part 14 to the reagent supply part 13 and the reagent can be supplied from the reagent supply part 13. In addition, in the present embodiment, a gas can be directly supplied from the first gas supply part 14 to the reagent introduction tube 17 not through the reagent supply part 13. In this case, not the reagent but the gas is supplied through the reagent introduction tube 17 into the conversion vessel 11, and thus, the interior of the conversion vessel 11 can be pressurized. Such switchover of a gas supply manner can be performed, for example, by operating a flow channel switchover mechanism including a three-way valve.

The second gas supply part 15 can supply a gas into the conversion vessel 11 via the reagent discharge tube 18. The gas supplied from the second gas supply part 15 is an inert gas such as nitrogen gas. Note that the gas supplied from the second gas supply part 15 is not limited to nitrogen gas as long as the gas is an inert gas, and may be another gas such as helium gas or argon gas.

The gas supplied from the second gas supply part 15 may be of the same kind as the gas supplied from the first gas supply part 14, or may be of a different kind. The pressure of the gas supplied from the first gas supply part 14 and the pressure of the gas supplied from the second gas supply part 15 are preferably set to values different from each other.

Figure 2:
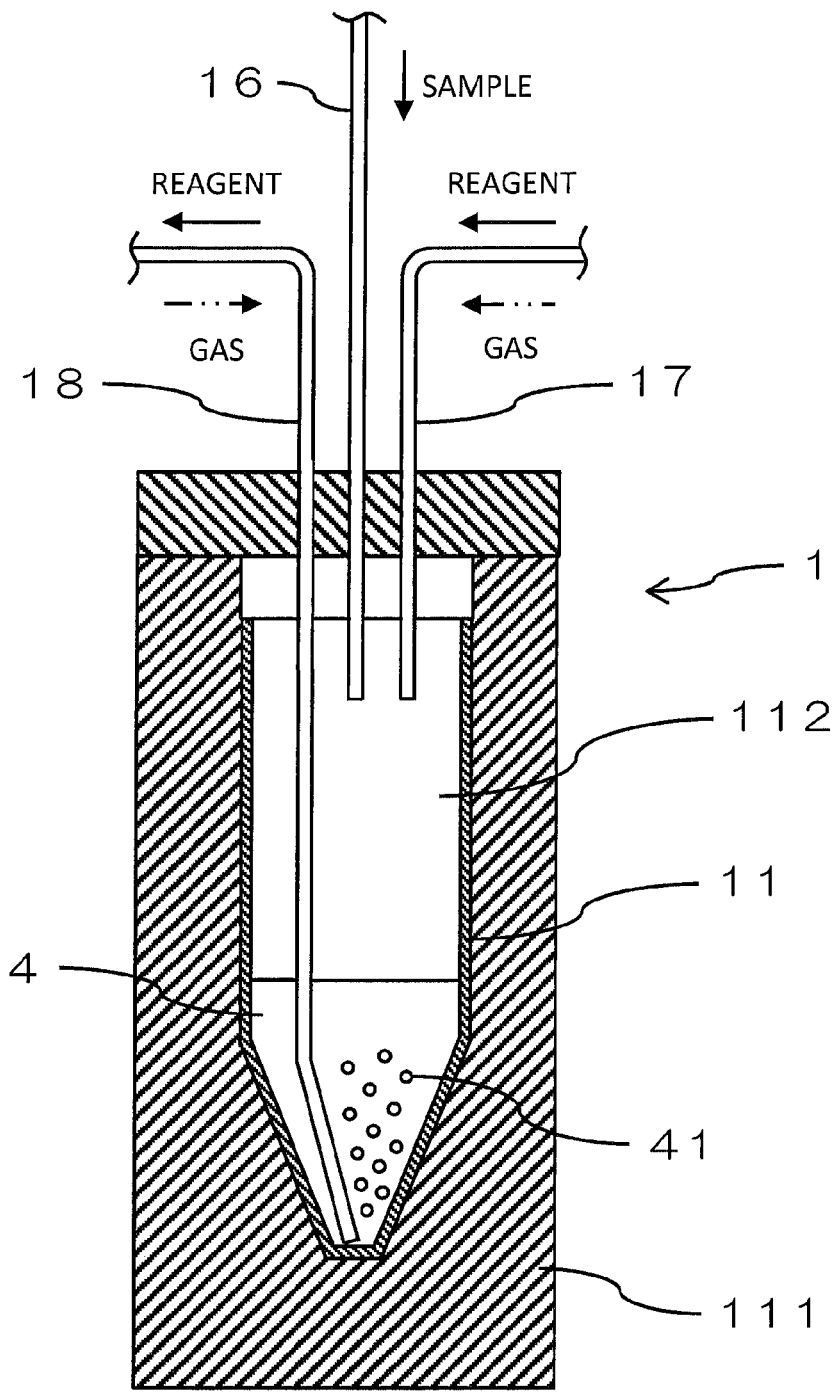
FIG. 2 is a schematic cross-sectional view illustrating a configuration example around a conversion vessel.

FIG. 2 is a schematic cross-sectional view illustrating a configuration example around the conversion vessel 11. The conversion vessel 11 is accommodated in a state of being sealed in a heat block 111, and is heated to a set temperature (for example, about 60° C.) by the heat block 111. Note that the heat block 111 can be omitted.

Ends of the sample introduction tube 16, the reagent introduction tube 17, and the reagent discharge tube 18 are inserted into the conversion vessel 11. The ends of the sample introduction tube 16 and the reagent introduction tube 17 are located at an upper portion inside the conversion vessel 11, and are located higher than the liquid surface of the reagent 4 supplied into the conversion vessel 11. In contrast, the end of the reagent discharge tube 18 is located at a bottom portion inside the conversion vessel 11, and is located lower than the liquid surface of the reagent 4 supplied into the conversion vessel 11. Note that even though not illustrated in FIG. 2, an end of a vent tube for exhausting the gas in the conversion vessel 11 into atmosphere may be inserted into the conversion vessel 11.

The amino acid sample (ATZ-amino acid) is introduced from the sample introduction tube 16 into the conversion vessel 11. In addition, the reagent 4 is introduced from the reagent introduction tube 17 into the conversion vessel 11, and therefore the amino acid sample is stabilized and the stabilized amino acid sample (PTH-amino acid) is dissolved in the reagent 4 at the bottom portion inside the conversion vessel 11. Then, a gas is supplied from the first gas supply part 14 into the conversion vessel 11 via the reagent introduction tube 17, and thus air in space 112 above the reagent 4 in the conversion vessel 11 is pressurized.

In this state, a gas is supplied from the second gas supply part 15 into the conversion vessel 11 via the reagent discharge tube 18. Thus, the gas is supplied into the reagent 4 from the end of the reagent discharge tube 18 located at the bottom portion inside the conversion vessel 11. As a result, gas bubbles 41 are formed in the reagent 4.

After such a process of forming gas bubbles 41 in the reagent 4 has been performed for only a predetermined time period, the reagent is discharged to the outside of the conversion vessel 11 from the reagent discharge tube 18. At that time, the reagent is discharged from the end of the reagent discharge tube 18 located at the bottom portion inside the conversion vessel 11, and therefore all of the reagent in the conversion vessel 11 can be discharged to the outside.

In the present embodiment, a gas is supplied into the reagent 4 in the conversion vessel 11 from the second gas supply part 15, and thus gas bubbles 41 are formed in the reagent 4 and the gas bubbles 41 promote volatilization of the organic solvent in the reagent 4. Thus, the organic solvent is volatilized in the space 112 above the reagent 4 in the conversion vessel 11, and concentration of the organic solvent in the reagent 4 can be easily and efficiently lowered. In addition, differing from the configuration of completely drying an amino acid sample (PTH-amino acid) and then adding a solvent for a HPLC, which is a conventional method, since the amino acid sample does not adhere to an inner surface of the conversion vessel 11, occurrence of sample loss can be prevented.

It is considered that since the area of the gas-liquid interface in the reagent 4 increases in a case of forming gas bubbles in the reagent 4 as described above, volatilization of the organic solvent is promoted via the interface.

In addition, in the present embodiment, a gas is supplied into the reagent 4 in the conversion vessel 11 via the reagent discharge tube 18 for discharging the reagent 4 in which the amino acid sample (PTH-amino acid) is dissolved to the outside of the conversion vessel 11, and therefore gas bubbles 41 can be formed in the reagent 4. Since the reagent discharge tube 18 is usually configured to discharge the reagent 4 from the bottom portion inside the conversion vessel 11 in the same manner as in the present embodiment, gas bubbles 41 can be formed from lower part of the reagent 4 if a gas is supplied into the conversion vessel 11 via the reagent discharge tube 18.

Therefore, since gas bubbles 41 can be favorably formed in the reagent 4, concentration of the organic solvent in the reagent 4 can be efficiently lowered. In addition, since gas bubbles 41 can be formed in the reagent 4 without adding a new configuration, concentration of the organic solvent in the reagent 4 can be easily lowered without incurring a cost increase.

Furthermore, in the present embodiment, a gas is supplied into the conversion vessel 11 via the reagent introduction tube 17 for introducing the reagent 4 into the conversion vessel 11, and thus the interior of the conversion vessel 11 can be pressurized. Since the reagent introduction tube 17 is usually configured to introduce a reagent into the conversion vessel 11 by pressure of a gas in the same manner as in the present embodiment, the interior of the conversion vessel 11 can be pressurized without newly adding a configuration if a gas is supplied into the conversion vessel 11 via the reagent introduction tube 17.

Referring again to FIG. 1, the control device 3 is configured of a computer, for example, and includes a control unit 31, an operation unit 32, a display unit 33, and the like. The control unit 31 is configured to include a CPU (Central Processing Unit), for example. The CPU executes a program, which causes the control unit 31 to function as a gas supply control unit 311, a setting reception processing unit 312, an analysis processing unit 313, or the like.

The operation unit 32 is configured of, for example, a keyboard and a mouse, and an operator can perform various setting operations by using the operation unit 32. The display unit 33 is configured of, for example, a liquid crystal display, and the operator can confirm the operation settings and the operation status of the analyzer by viewing display of the display unit 33.

The gas supply control unit 311 controls gas supply from the first gas supply part 14 and from the second gas supply part 15. Specifically, by controlling the opening or closing state of a valve (not illustrated) provided to each of the first gas supply part 14 and the second gas supply part 15, the gas supply state from each of the first gas supply part 14 and the second gas supply part 15 is switched over.

The setting reception processing unit 312 receives settings regarding gas supply from the first gas supply part 14 and from the second gas supply part 15. In the present embodiment, the operator can set a time period for supplying a gas from each of the first gas supply part 14 and the second gas supply part 15 by operating the operation unit 32. The gas supply control unit 311 controls gas supply from each of the first gas supply part 14 and the second gas supply part 15 according to the set time period received by the setting reception processing unit 312 such that a gas is supplied only for the set time period.

As described, in the present embodiment, since the time period for supplying a gas from the second gas supply part 15 can be arbitrarily set, the time period for forming gas bubbles 41 in the reagent 4 can be adjusted by adjusting the set time period, and concentration of the organic solvent in the reagent 4 can be arbitrarily adjusted. At that time, since the time period for supplying a gas from the first gas supply part 14 can also be arbitrarily set, the interior of the conversion vessel 11 can be favorably pressurized in accordance with the time period for forming gas bubbles 41.

The analysis processing unit 313 identifies each sample component separated while passing through the column 21 according to the detection signal from the detector 22, and analyzes the amino acid sequence of the target protein sample. The analysis result obtained by the analysis processing unit 313 is displayed on the display unit 33, and thus the operator is notified of the result. Note that the analysis result obtained by the analysis processing unit 313 is not limited to the configuration in which the result is displayed on the display unit 33, and may be, for example, a configuration in which the result is output in another manner such as printing.

Figure 3A:
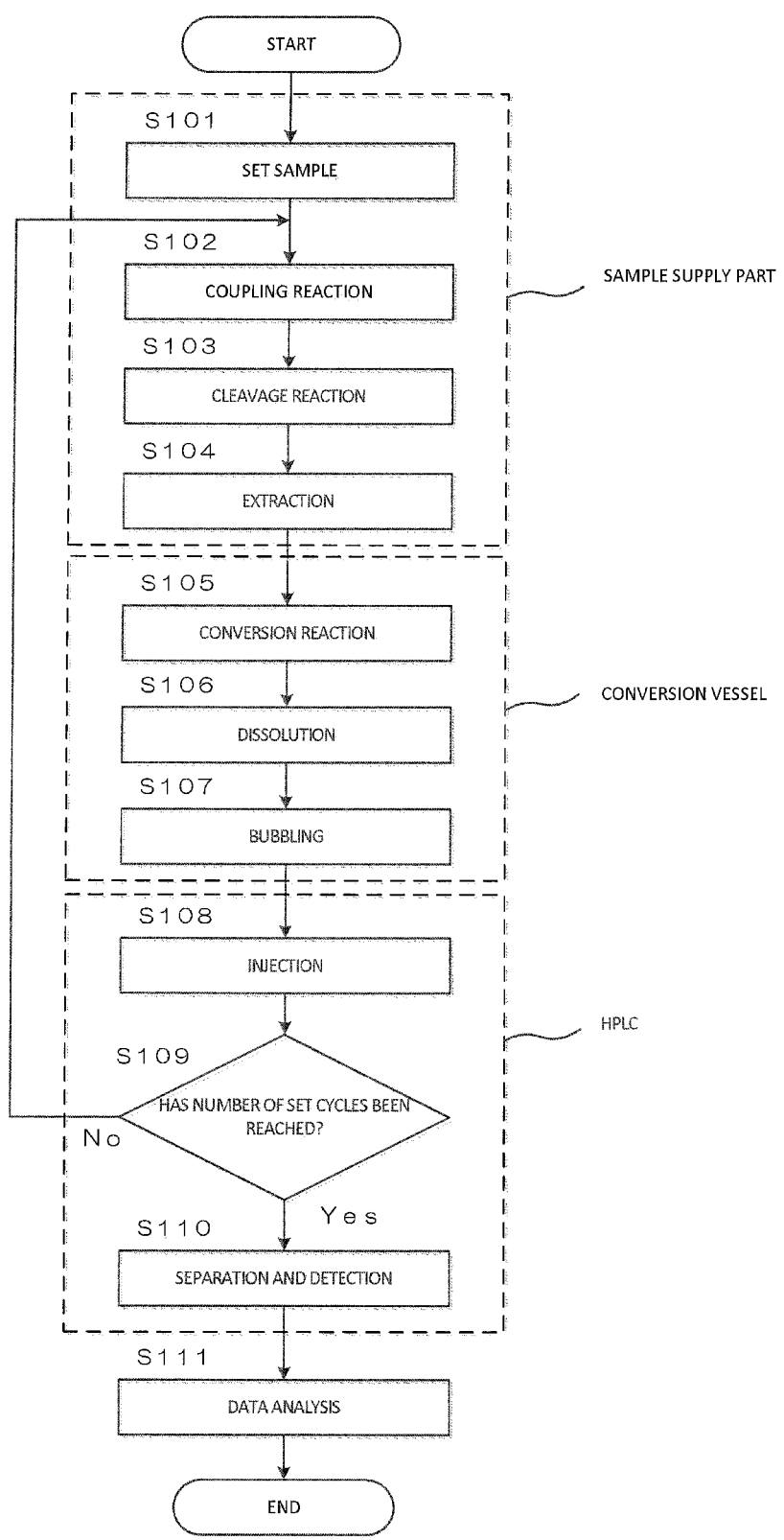
FIG. 3A is a flowchart illustrating a flow of processes when an analysis of a protein sample is performed by the analyzer illustrated in FIG. 1.

FIG. 3A is a flowchart illustrating a flow of processes performed when a protein sample is analyzed by the analyzer illustrated in FIG. 1. When an analysis is started, first, the sample holder holding a protein sample is set in the sample supply part 12 (step S101), and then a coupling reaction is performed (step S102).

In the coupling reaction, for example, trimethylamine is supplied from the reagent supply part 13 to the sample supply part 12, a reaction chamber of the sample supply part 12 is filled with trimethylamine (gas), and then, a PITC n-heptane solution is supplied from the reagent supply part 13 into the reaction chamber, the solution is reacted with an N-terminal amino group of protein, and thus PTC-protein is generated. Then, ethyl acetate is supplied from the reagent supply part 13 into the reaction chamber to wash out excess reagent and a by-product.

Thereafter, trifluoroacetic acid is supplied from the reagent supply part 13 into the reaction chamber, and thus the N-terminal peptide bond of PTC-protein is cleaved, and an ATZ-amino acid is generated (step S103: cleavage reaction). The cleavaged ATZ-amino acid is extracted by supplying n-butyl chloride into the reaction chamber from the reagent supply part 13, and the extracted amino acid sample (ATZ-amino acid) is introduced into the conversion vessel 11 from the sample supply part 12 (step S104).

Next, a conversion reaction is performed in the conversion vessel 11 (step S105). In the conversion reaction, for example, a trifluoroacetic acid solution is introduced from the reagent supply part 13 into the conversion vessel 11, and thus the ATZ-amino acid is converted into a stable PTH-amino acid. Then, a mixed solution of acetonitrile and water is supplied from the reagent supply part 13 into the conversion vessel 11, and thus the PTH-amino acid is dissolved in the mixed solution (step S106). This step S106 constitutes a dissolution step of dissolving the sample (amino acid sample) into the reagent 4 containing the organic solvent.

A bubbling process as described with reference to FIG. 2 is performed for the reagent 4 in the conversion vessel 11 (step S107). Thereafter, the reagent 4 in the conversion vessel 11 is discharged from the reagent discharge tube 18 to the HPLC 2, and is injected into the column 21 of the HPLC 2 (step S108). The processes in steps S102 to S108 are repeated until the number of cycles set in advance is reached (Yes in step S109), and the amino acid sample (PTH-amino acid) separated in the column 21 is detected by the detector 22 (step S110). Then, the detection signal from the detector 22 is analyzed by the analysis processing unit 313, and thus data display and record, identification, quantification, yield calculation, or the like of the PTH-amino acid are performed (step S111).

Figure 3B:
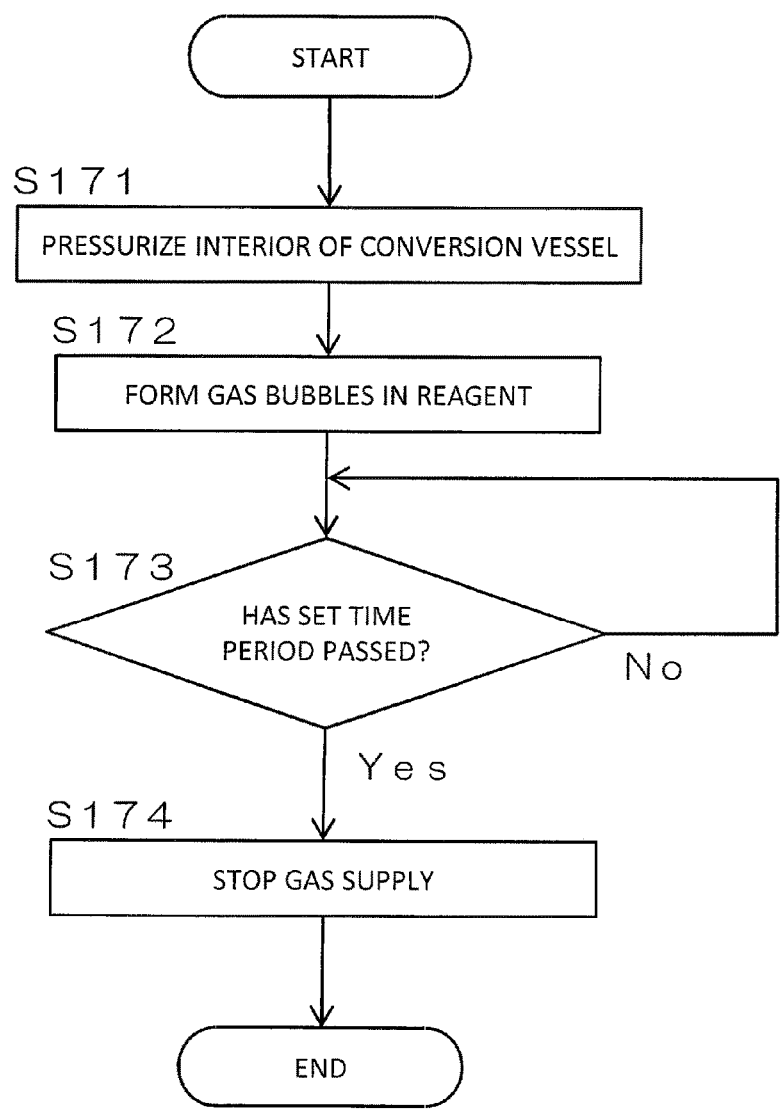
FIG. 3B is a flowchart illustrating an example of a bubbling process.

FIG. 3B is a flowchart illustrating an example of the bubbling process. In the bubbling process illustrated in step S107 in FIG. 3A, first, a gas is supplied from the first gas supply part 14 into the conversion vessel 11 via the reagent introduction tube 17, and thus the interior of the conversion vessel 11 is pressurized (step S171: first gas supply step). In addition, a gas is supplied from the second gas supply part 15 into the conversion vessel 11 via the reagent discharge tube 18, and thus gas bubbles 41 are formed in the reagent 4 in the conversion vessel 11 (step S172: second gas supply step). This state is maintained, and thus concentration of the organic solvent in the reagent 4 gradually lowers.

Then, when a time period set in advance as the time period for supplying a gas from each of the first gas supply part 14 and the second gas supply part 15 has passed (Yes in step S173), gas supply from each of the first gas supply part 14 and the second gas supply part 15 is stopped (step S174: gas supply stop step), and the reagent 4 is discharged from the reagent discharge tube 18 to the HPLC 2 (reagent discharge step). The time period for supplying a gas from the first gas supply pare 14 and the bane period for supplying a gas from the second gas supply part 15 may be identical or different from each other. In addition, the time period for supplying a gas from the first gas supply part 14 and the time period for supplying a gas from the second gas supply part 15 may be set separately. Alternatively, one of the time periods may be set first and then the other may be set with reference to the time period set first.

Hereinafter, the results of the experiments conducted in order to confirm the effects of the present invention will be described. In the experiments, 50 µL of a reagent with concentration of 0.5 µmol/µL obtained by using acetonitrile as an organic solvent and mixing and diluting acetonitrile with water was supplied to an amino acid sample (PTH-amino acid) in the conversion vessel 11.

Figure 4A:
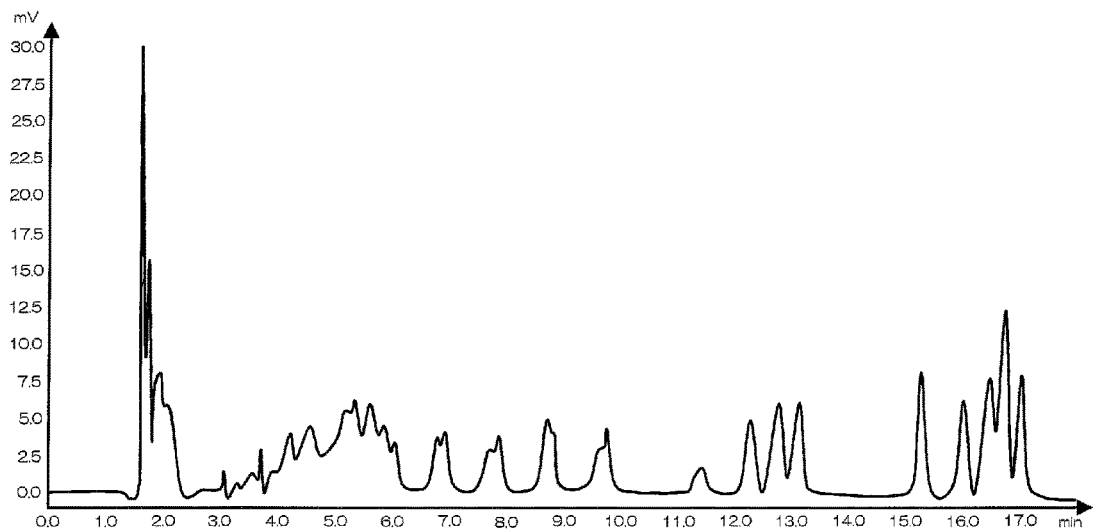
FIG. 4A is a diagram illustrating a detection result in a case where an analysis of a protein sample is performed by using a conventional analyzer.
Figure 4B:
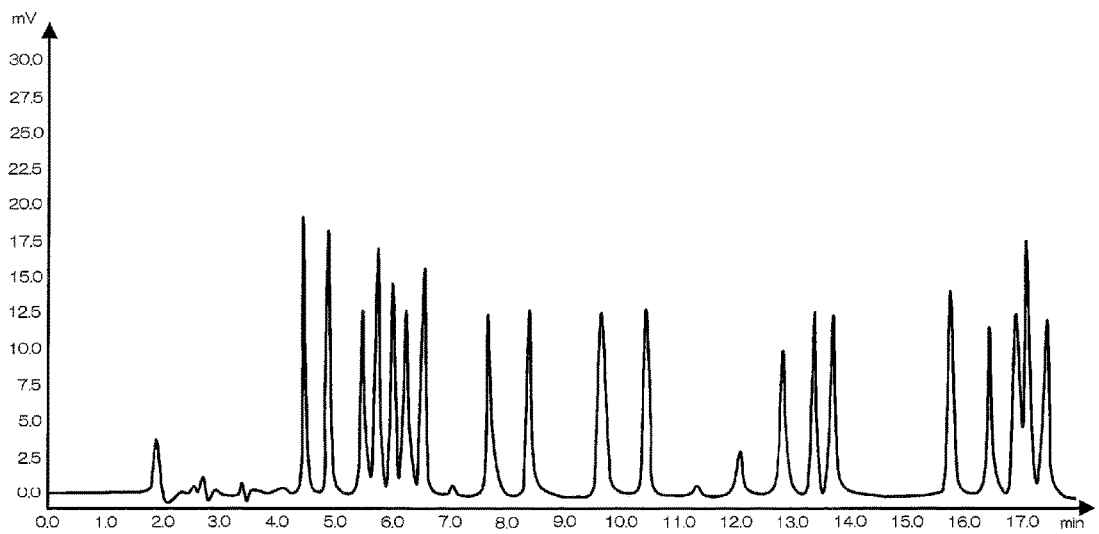
FIG. 4B is a diagram illustrating a detection result in a case where an analysis of the protein sample is performed by using the analyzer according to the present invention.

FIG. 4A is a diagram illustrating the detection result in a case where an analysis of a protein sample was performed by using a conventional analyzer. FIG. 4B is a diagram illustrating the detection result in a case where an analysis of the protein sample was performed by using the analyzer according to the present invention. In the experiment illustrated in FIG. 4B, in a state where the interior of the conversion vessel 11 was pressurized by supplying a gas into the conversion vessel 11 from the first gas supply part 14, a gas was supplied for 24 seconds from the second gas supply part 15 into the conversion vessel 11 via the reagent discharge tube 18, thereby forming gas bubbles 41 in the reagent 4 in the conversion vessel 11 during that period.

In a case where the conventional analyzer configured to add a solvent for a HPLC after completely drying an amino acid sample (PTH-amino acid) was used, as illustrated in FIG. 4A, peaks which cannot be favorably separated exist in the former part. This is considered to be due to high concentration of the organic solvent. In contrast, in a case where the analyzer according to the present invention was used, as illustrated in FIG. 4B, since there is no peak which cannot be favorably separated, it can be seen that concentration of the organic solvent favorably lowered, and the analysis result was improved.

In the above embodiment, the sample introduction part which introduces an amino acid sample (ATZ-amino acid) into the conversion vessel 11 is configured of the sample introduction tube 16 inserted into the upper portion inside the conversion vessel 11; however, the sample introduction part is not limited to this. For example, an amino acid sample may be introduced by using a member other than a tube. In addition, the reagent introduction part which introduces the reagent 4 into the conversion vessel 11 is not limited to the reagent introduction tube 17 inserted into the upper portion inside the conversion vessel 11. For example, the reagent 4 may be introduced by using a member other than a tube. Furthermore, the reagent discharge part which discharges the reagent 4 from the conversion vessel 11 is not limited to the reagent discharge tube 18 inserted into the bottom portion inside the conversion vessel 11. For example, the reagent 4 may be discharged by using a member other than a tube.

In addition, in the above embodiment, the configuration where a gas is supplied from the first gas supply part 14 into the conversion vessel 11 via the reagent introduction tube 17 has been described; however, the present invention is not limited to this. A configuration may be adopted where a gas is supplied into the conversion vessel 11 via a path provided separately from the reagent introduction tube 17. In this case, the present invention is not limited to the configuration where the first gas supply part 14 can supply a gas also to the reagent supply part 13. The first gas supply part 14 may be dedicated to pressurizing the interior of the conversion vessel 11. The present invention is not limited to the configuration where a gas is supplied from the second gas supply part 15 into the reagent 4 in the conversion vessel 11 via the reagent discharge tube 18. A configuration may be adopted where a gas is supplied into the reagent 4 in the conversion vessel 11 via a path separately provided from the reagent discharge tube 18.

Furthermore, in the above embodiment, the configuration where the device 1 for pretreatment of a sample is provided in the protein sequencer has been described; however, the present invention is not limited to be applied to a protein sequencer which analyzes a protein sample, and can be applied also to the device 1 for pretreatment of a sample included in another analyzer. In addition, the present invention is not limited to a device which automatically performs processing for a protein sample, such as a protein sequencer, and the present invention can also be applied to a configuration where at least some of the processes are performed manually by an operator.

DESCRIPTION OF REFERENCE SIGNS 1 device for pretreatment of a sample
2 HPLC
3 control device
4 reagent
11 conversion vessel
12 sample supply part
13 reagent supply part
14 first gas supply part
15 second gas supply part
16 sample introduction tube
17 reagent introduction tube
18 reagent discharge tube
21 column
22 detector
31 control unit
32 operation unit

33 display unit
41 gas bubble
111 heat block
112 space
311 gas supply control unit
312 setting reception processing unit
313 analysis processing unit

The invention claimed is:

1. A method for pretreatment of a sample comprising:
a dissolution step of introducing a reagent containing an organic solvent into a vessel, and dissolving the sample in the reagent to form a sample-containing-reagent;
a sample supply step of subjecting a protein to an Edman degradation, obtaining an amino acid from the protein by the Edman degradation, and introducing the obtained amino acid as the sample into the vessel;
a gas supply step of supplying a first gas into the vessel outside the sample-containing-reagent, and thus pressurizing an interior of the vessel, and supplying a second gas into the sample-containing-reagent in the vessel and thus forming a gas bubble in the sample-containing-reagent to volatilize the sample-containing-reagent while the first gas is supplied to put an inside of the vessel in a high pressure state; and
an analyzing step of analyzing the sample after the gas supply step,
wherein the first gas and the second gas supplied by the gas supply step are an inert gas, and
wherein a pressure of the first gas supplied from the gas supply step and a pressure of the second gas supplied from the gas supply step are set to values different from each other.

2. The method for pretreatment of a sample according to claim 1, wherein the inert gas is nitrogen gas, helium gas or argon gas.

3. The method for pretreatment of a sample according to claim 1, further comprising a reagent discharging step using a reagent discharge part of discharging a sample-containing-reagent in which the sample is dissolved in the vessel to an outside of the vessel, wherein one end of the reagent discharge part is located at a bottom portion inside the vessel, and is configured to be in direct contact with the reagent.

4. The method for pretreatment of a sample according to claim 1, further comprising: a setting reception processing step of receiving settings regarding a supply of the first gas and the second gas from the gas supply step; and
a gas supply control step which controls the supply of the first gas and the second gas from the gas supply step according to a set time period received by the setting reception processing step such that the first gas and the second gas are supplied only for the set time period.

5. The method for pretreatment of a sample according to claim 1, wherein a time period for supplying the first gas and a time period for supplying the second gas are different from each other.

\* \* \* \* \*